(12) United States Patent
Yamazaki et al.

(10) Patent No.: US 6,339,721 B1
(45) Date of Patent: Jan. 15, 2002

(54) BRAIN WAVE DATA PROCESSING DEVICE AND STORAGE MEDIUM

(75) Inventors: Toshimasa Yamazaki; Akihisa Kenmochi, both of Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 09/421,271

(22) Filed: Oct. 20, 1999

(30) Foreign Application Priority Data

Oct. 28, 1998 (JP) .......................................... 10-321378

(51) Int. Cl.[7] .............................................. A61B 5/00
(52) U.S. Cl. ...................................................... 600/544
(58) Field of Search ............................. 600/300, 544, 600/545

(56) References Cited

U.S. PATENT DOCUMENTS

| 5,282,474 A | * | 2/1994 | Valdes Sosa et al. | ........ 600/544 |
| 5,797,840 A | * | 8/1998 | Akselrod et al. | ............ 600/301 |
| 5,995,868 A | * | 11/1999 | Dorfmeister et al. | ....... 600/545 |

OTHER PUBLICATIONS

Masatoshi Nakamura et al., "Single Sweep Record of P300 by Using Wavelet Transofrom", Nov. 23, 1996, pp. 355–358 with English Abstract.

* cited by examiner

*Primary Examiner*—Robert L. Nasser
(74) *Attorney, Agent, or Firm*—Sughrue Mion, PLLC

(57) ABSTRACT

A wavelet conversion means (13) for subjecting brain wave data in a single trial to wavelet conversion, a wavelet coefficient window means (15) for extracting a predetermined area by a wavelet coefficient window from a wavelet coefficient surface obtained by the wavelet conversion, and a brain wave data discriminating means (17) for discriminating brain wave data by judging whether or not the predetermined area is extracted are provided to automate the work to extract distinguishing patterns from individual (in a single trial) brain wave data and to obtain averaging of the brain wave data. By considering whole of wavelet conversion coefficients, averaging and extraction of a vertex latency of distinguishing patterns can be executed without significantly losing the information of original waveform data.

9 Claims, 14 Drawing Sheets

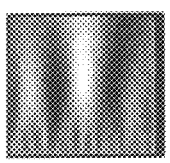 Trial #21
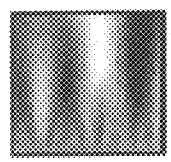 Trial #22
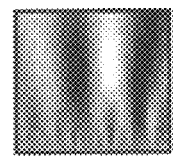 Trial #23
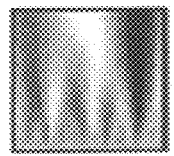 Trial #24
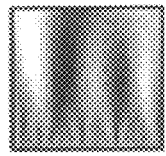 Trial #25
FIG. 23B  FIG. 24B  FIG. 25B  FIG. 26B  FIG. 27B
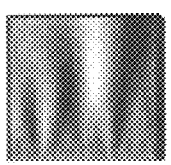 Trial #26
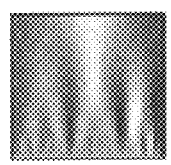 Trial #27
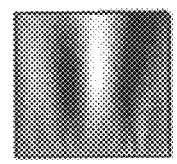 Trial #28
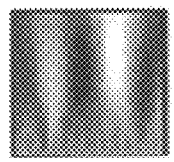 Trial #29
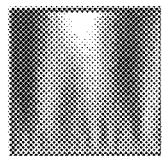 Trial #30
FIG. 28B  FIG. 29B  FIG. 30B  FIG. 31B  FIG. 32B
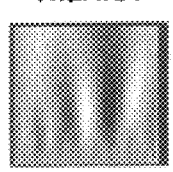 Trial #31
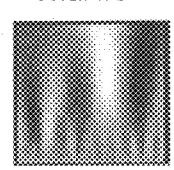 Trial #32
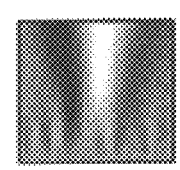 Trial #33
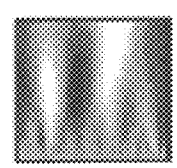 Trial #34
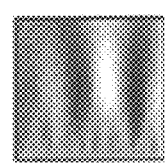 Trial #35
FIG. 33B  FIG. 34B  FIG. 35B  FIG. 36B  FIG. 37B
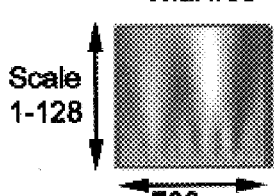 Trial #36 (Scale 1-128, 700ms)
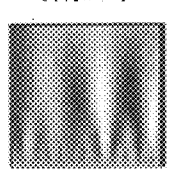 Trial #37
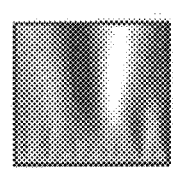 Trial #38
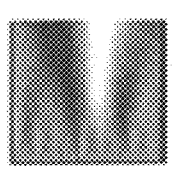 Trial #39
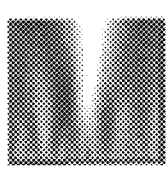 Trial #40
FIG. 38B  FIG. 39B  FIG. 40B  FIG. 41B  FIG. 42B

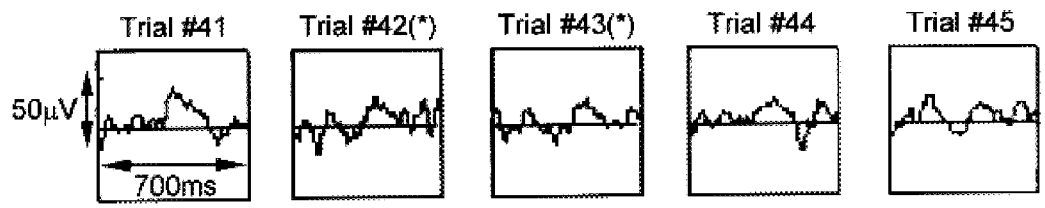
FIG. 43A    FIG. 44A    FIG. 45A    FIG. 46A    FIG. 47A
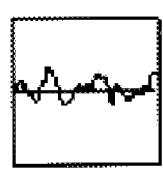 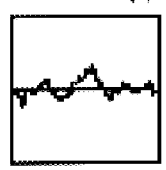   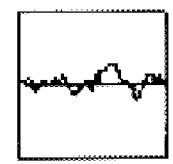
FIG. 48A    FIG. 49A    FIG. 50A    FIG. 51A    FIG. 52A
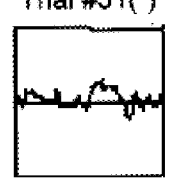
FIG. 53A
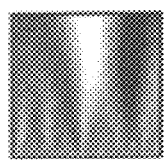 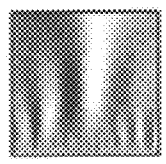 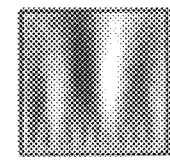 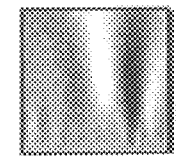 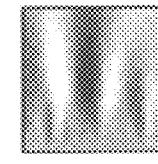
FIG. 43B    FIG. 44B    FIG. 45B    FIG. 46B    FIG. 47B
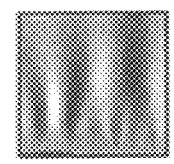 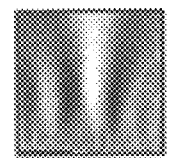 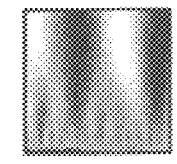 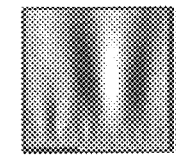 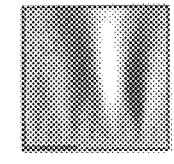
FIG. 48B    FIG. 49B    FIG. 50B    FIG. 51B    FIG. 52B
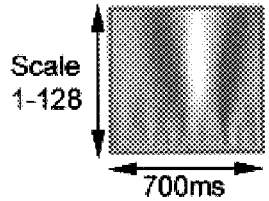
FIG. 53B Example of a signal plane (Session 1, Trial #28)

ERP & Ca, b Session 1 : Trial #28
The potential difference of the waveform is depicted with ±50 μV.)

BRAIN WAVE DATA PROCESSING DEVICE AND STORAGE MEDIUM

CROSS REFERENCE TO RELATED APPLICATIONS

The present invention claims priority from Japanese Patent Application No. 10-321378 filed Oct. 28, 1999, the contents of which are incorporated herein by reference.

BACKGROUND OF THE INVENTION

1. Field of the Invention

The present invention relates to a brain wave data processing device used for processing brain wave data to detect distinctive patterns, and more particularly to a brain wave data processing device which averages brain wave data in which distinguishing patterns are detected in individual brain wave data obtained in a single trial, and to a computer readable storage medium in which a program to realize this brain wave data processing device is loaded.

2. Description of Related Art

When an excitation or event is added to a subject (trial), an electric potential evoked by the added excitation or event (evoked potential) would occur in the brain and spinal cord of the subject. In particular, a potential variation occurred in a cerebral cortex with a constant time relation to an excitation or event is referred to as an event-related potential (ERP). Such a potential or potential variation is generally observed as brain wave data, and used as effective data to know the mechanism of, for example, feeling, perception, and psychological phenomenon, or to find a position of an injury. However, the amplitude of the potential variations involved with the trial is considerably smaller than that of rhythmic, ordinary brain waves, so that a signal occurred from one observation is often indistinct. Therefore, a method has been devised in which multiple trials are performed under the same conditions and the brain wave data obtained from each trial are added and averaged with the time of excitation (event) as a reference point, causing components of the rhythmic, ordinary brain waves to be canceled, so that only the evoked potential obtained by the excitation (event) is extracted. This technique is referred to as an averaging method.

Incidentally, as a technique to process an unsteady signal which changes over time to analyze whether or not a distinguishing component is included, in these days, attention has focused on the wavelet conversion. An example of the brain wave data subjected to the wavelet conversion in a single trial includes the reference "P300 Single Trial Storage Processing Based on Wavelet Conversion" by Masatoshi Nakamura, Yasushi Hisatomi, Naoshi Sugikou, Shigeto Nishida, Yoshio Ikeda, and Hiroshi Shibasaki (Proceedings of the fifteenth SICE Kushu branch congress, pp. 355–358, Nov. 23, 1996). However, the device by Nakamura et al. provides only the wavelet conversion and inverse wavelet conversion with respect to the brain wave data, and includes only the filtering function to eliminate noises in live data. Further, although they have attempted to restrict parameters included in the wavelet conversion according to the result of filtering to the live data, the reliability of the result can not be expected, because they use a formula model as a true waveform. In addition, they have examined wavelet conversion parameters only in limited ranges, so that a considerable amount of information contained in the live data may have been lost. The largest problem of the report by Nakamura et al. is that how to use the waveforms subjected to filtering process (the waveform data subjected to the wavelet conversion and inverse wavelet conversion) is not mentioned. After all, the device by Nakamura et al. may be considered not to reach the practical stage yet, although the attempt to analyze the brain wave data using the wavelet conversion and inverse wavelet conversion can be found.

SUMMARY OF THE INVENTION

When the averaging of the brain wave data is determined by the averaging method and the evoked potential, such as the event-related potential (ERP), is observed, in the past, an enormous period of time was required in order to extract distinguishing patterns from individual brain wave data to obtain the averaging of the brain wave data. The reason for it is that the work of extracting the patterns was all performed by the inspection of an experimenter (or a decipherer of the brain wave).

It is an object of the present invention to provide a method for analyzing brain wave data which can automate the work to extract distinguishing patterns from brain wave to reduce the load of the experimenter and improve the quality and reliability of the brain wave data obtained as well as the efficiency of the work for analyzing the brain wave data.

In addition, as described above, in the past, a concrete application of the wavelet conversion for the brain wave data was not made clear, however, it is also another object of the present invention to exhibit concrete applications. Accordingly, the present invention exhibits the averaging of the brain wave data as a concrete application of the wavelet conversion, and also it is an object of the present invention to provide a device which performs the averaging without significantly losing the information of original waveform data by considering not only the waveform data itself as with the prior art but also whole of values of the wavelet conversion parameters, when the results of the wavelet conversion are compared and examined.

The brain wave data processing device according to the present invention comprises, in a brain wave data processing device detecting distinguishing patterns from individual brain wave data obtained in a single trial, a brain wave data storage means for storing digital brain wave data, a wavelet conversion means for subjecting the digital brain wave data read out from the brain wave data storage means to wavelet conversion to determine a wavelet coefficient, a wavelet coefficient surface output means for outputting the wavelet coefficient as function values of a scale parameter and a shift parameter in the wavelet conversion, a wavelet coefficient window parameter setting means for setting a wavelet coefficient window, a wavelet coefficient window means for extracting a predetermined area based on the wavelet coefficient window from a wavelet coefficient surface defined by the scale parameter, shift parameter, and wavelet coefficient, and a brain wave data discriminating means for discriminating whether or not the predetermined area has been extracted from the wavelet coefficient surface by the wavelet coefficient window means for individual digital brain wave data.

The brain wave data processing device according to the present invention may further be provided with a brain wave data averaging means for averaging only the digital brain wave data from which the predetermined area is extracted in the wavelet coefficient surface and a pattern latency extraction means for determining a vertex latency of distinguishing patterns included only in the digital brain wave data from which the predetermined area is extracted in the wavelet coefficient surface.

In the present invention, the brain wave data in which the distinguishing patterns have been detected, for example, by inspection are previously prepared and the corresponding wavelet coefficient surface is determined from these brain wave data, and the wavelet coefficient window may be set according to the shape and value of this wavelet coefficient surface. Although various types are considered as a mother wavelet in the wavelet conversion, Mexican Hat can be exhibited as a desirable one.

According to the present invention, the wavelet coefficient surface is the result of subjecting the brain wave data to the wavelet conversion, and by subjecting this wavelet coefficient surface to the wavelet coefficient window, it is discriminated whether or not a predetermined area is extracted in the wavelet coefficient surface, so that all the processing from the measurement of the brain wave data to the discrimination of whether distinguishing patterns exist in the brain wave data can be automatically performed.

Furthermore, by providing a brain wave data averaging means, all the processing from the measurement of the brain wave data to the averaging process can be automatically executed, and by providing a pattern latency extraction means, a vertex latency of the extracted pattern can be automatically determined.

BRIEF DESCRIPTION OF THE DRAWINGS

The present invention will hereinbelow be described with reference to the accompanying drawings, in which:

FIG. 3a to FIG. 53a show event-related potentials (ERPS) in single trials from the first trial to the twenty-first trial, and FIGS. 3b to FIG. 53b show the respective wavelet coefficient surface;

FIG. 55b shows a partially enlarged portion of FIG. 55a;

FIG. 59a shows brain wave data of a single trial and FIG. 59b shows a result of the wavelet coefficient calculated from the brain wave data of FIG. 59a.

DETAILED DESCRIPTION OF THE PREFERRED EMBODIMENTS

First Embodiment

Figure 1:
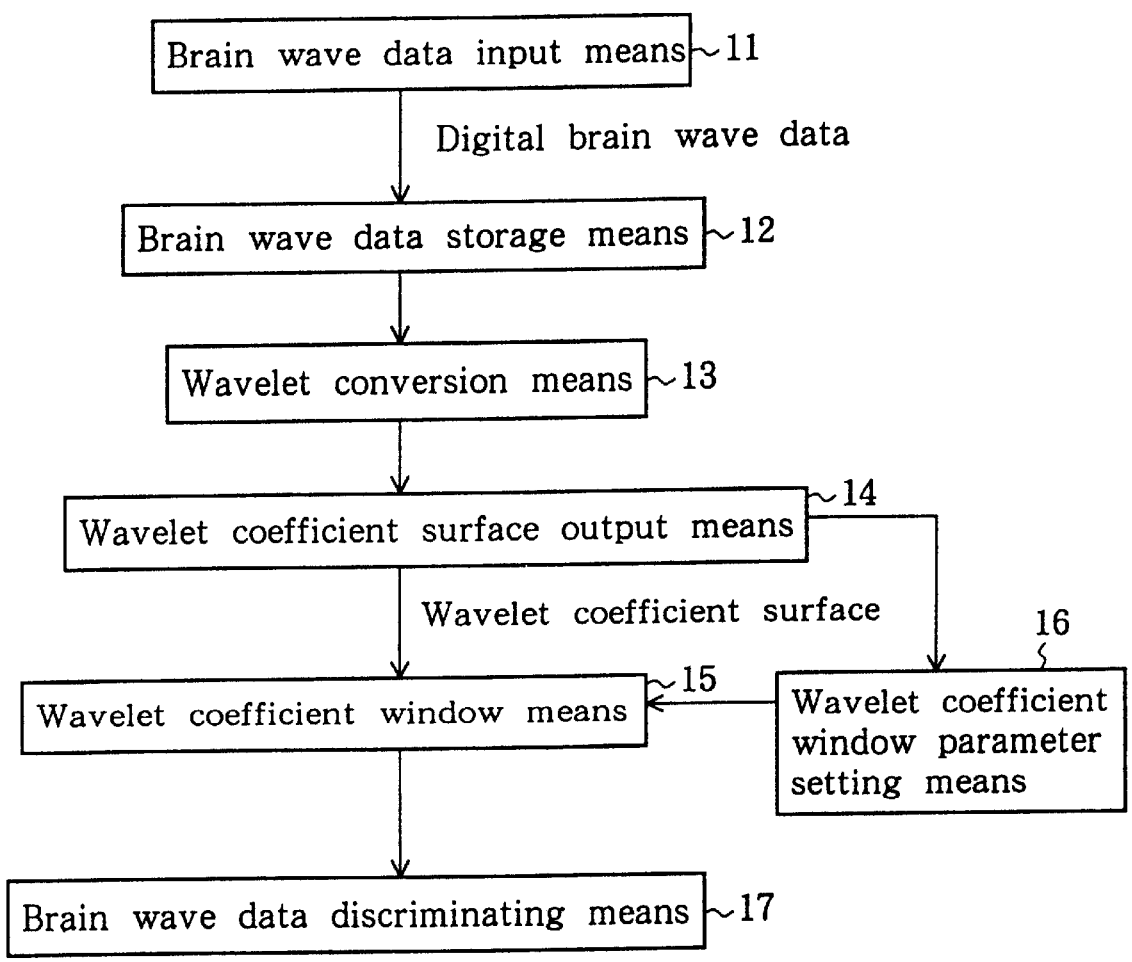
FIG. 1 is a block diagram showing a configuration of the brain wave data processing device of a first embodiment according to the present invention.

FIG. 1 is a block diagram showing a configuration of the brain wave data processing device of a first embodiment according to the present invention.

The brain wave data processing device comprises a brain wave data input means 11 to which a brain wave signal (analog brain wave data) from a subject is inputted and which subjects this brain wave signal to analog-digital conversion to make digital brain wave data, a brain wave data storage means 12 which stores the digital brain wave data obtained in the brain wave data input means 11, a wavelet conversion means 13 which reads out the digital brain wave data from the brain wave data storage means 12 to subject the read out digital brain wave data to wavelet conversion, a wavelet coefficient surface output means 14 which outputs a wavelet coefficient value obtained by the wavelet conversion in the wavelet conversion means 13 as a function value of a scale parameter and shift parameter included in the wavelet, a wavelet coefficient window means 15 which extracts a predetermined area (area corresponding to the wavelet coefficient window) in the function values outputted from the wavelet coefficient surface output means 14, a wavelet coefficient window parameter setting means 16 which sets up the wavelet coefficient window, and a brain wave data discriminating means 17 which discriminates whether the predetermined area is extracted by the wavelet coefficient window means 15 when the wavelet conversion means 13 subjects the individual brain wave data to the wavelet conversion, so that it is discriminated whether distinguishing patterns are included in the digital brain wave data.

In this case, the brain wave data storage means 12, the wavelet conversion means 13, the wavelet coefficient surface output means 14, the wavelet coefficient window means 15, the wavelet coefficient window parameter setting means 16, and the brain wave data discriminating means 17 may be constituted as separate hardware blocks to effect their functions, respectively, however, the functions can be typically realized in the block by the combination of one computer and a software program which is operated on this computer and corresponds to each means. In this application, these means are intended to be constituted by a computer and a computer program. As a computer in this case, a work station, a personal computer, or the like can be used. The inventors of the present invention used a personal computer, such as type PC-9821Xa, manufactured by NEC Corporation.

As a brain wave data input means 11, a configuration can be used comprising electrodes for brain wave, a living signal amplifier (for example, type 6R12 manufactured by NED Medical Systems Co.) which amplifies feeble signals measured by the electrodes for brain wave, and an A/D converter (for example, A/D conversion board type ADXM-98A manufactured by Kanohpus Electronics Co.) which converts analog brain wave data outputted from the living signal amplifier to digital brain wave data. The A/D conversion board in this case is inserted into an expansion slot of the personal computer and executes the analog-digital conversion by the control from the side of the personal computer. And also, the brain wave storage means 12 corresponds to a storage medium provided in the personal computer, such as, for example, a storage device integrated into a body of the personal computer, a magnet-optical disk, a floppy disk, or a removable hard disk. The wavelet conversion means 13 subjects the digital brain wave data read out from the brain wave storage means 12 to the wavelet conversion for predetermined channels and samples. A software executable on the personal computer to realize the wavelet conversion means 13 includes wavelet conversion software of Matlab Version 5.2 and Matlab Wavelet Tool Box 1.1.

Figures 3A, 4A, 5A, 6A, 7A:
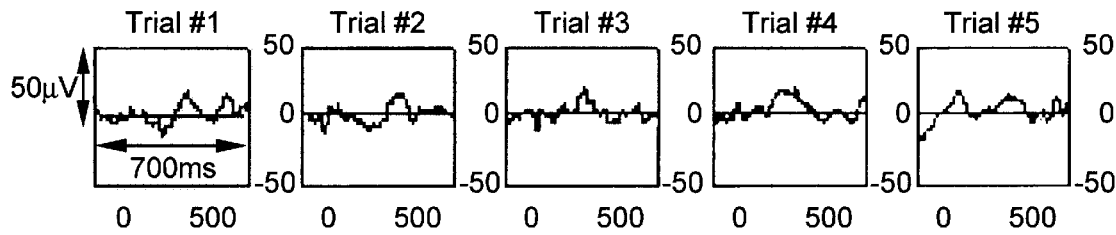
Figures 8A, 9A, 10A, 11A, 12A:
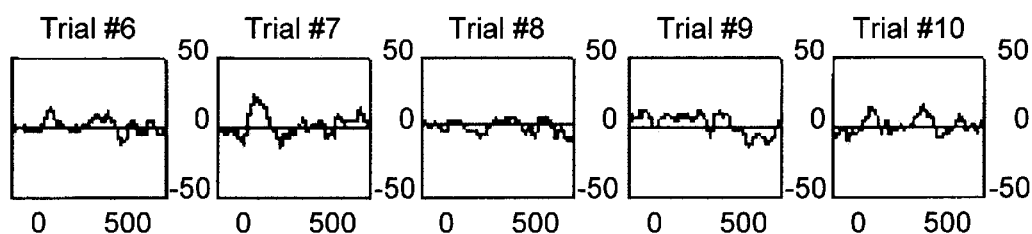
Figures 13A, 14A, 15A, 16A, 17A:
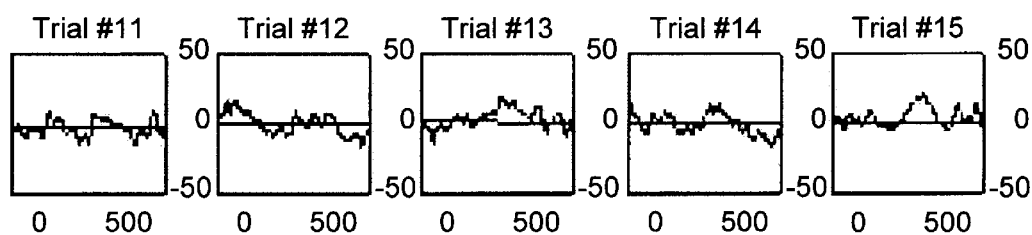
Figures 18A, 19A, 20A, 21A, 22A:
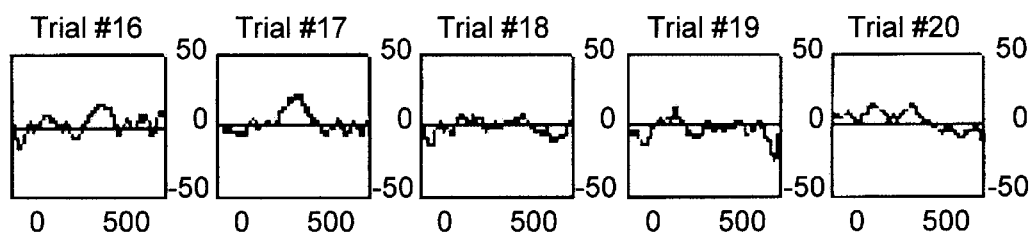
Figures 3B, 4B, 5B, 6B, 7B:
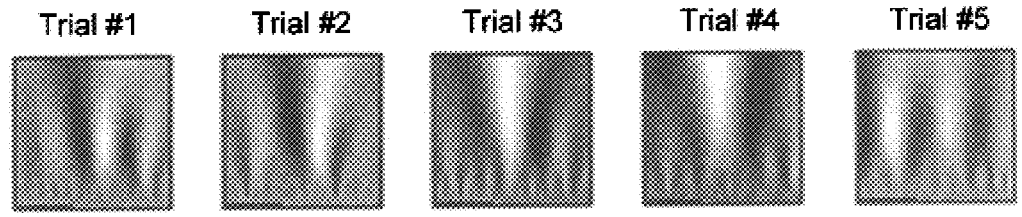
Figures 8B, 9B, 10B, 11B, 12B:
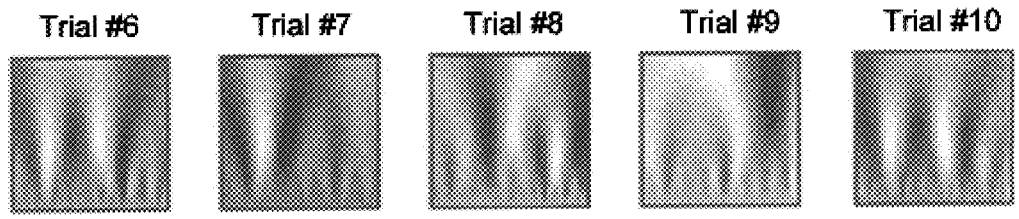
Figures 13B, 14B, 15B, 16B, 17B:
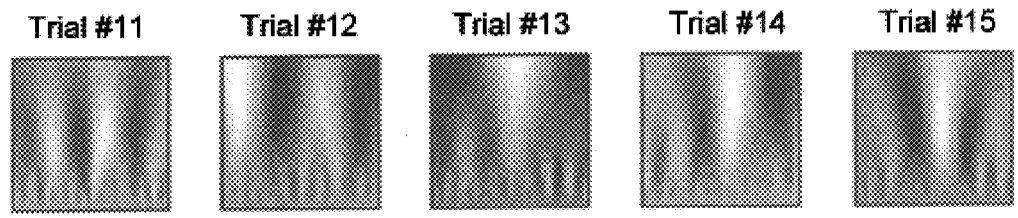
Figures 18B, 19B, 20B, 21B, 22B:
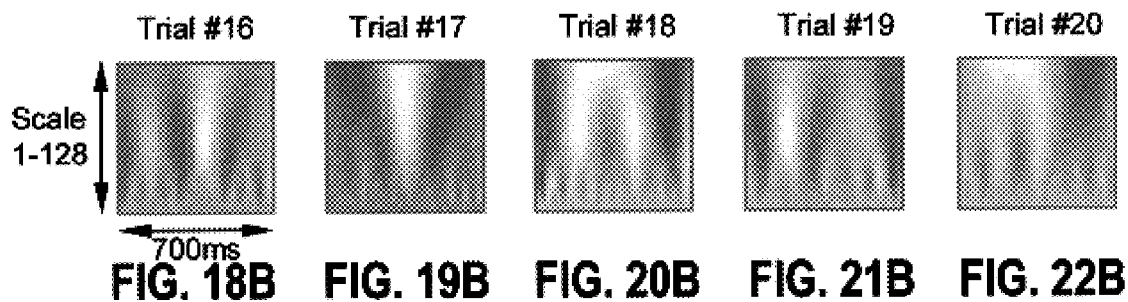
Figures 23A, 24A, 25A, 26A, 27A:
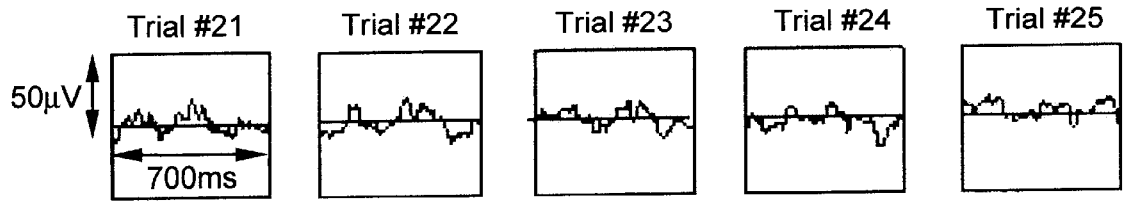
Figures 28A, 29A, 30A, 31A, 32A:
Figures 33A, 34A, 35A, 36A, 37A:
Figures 38A, 39A, 40A, 41A, 42A:
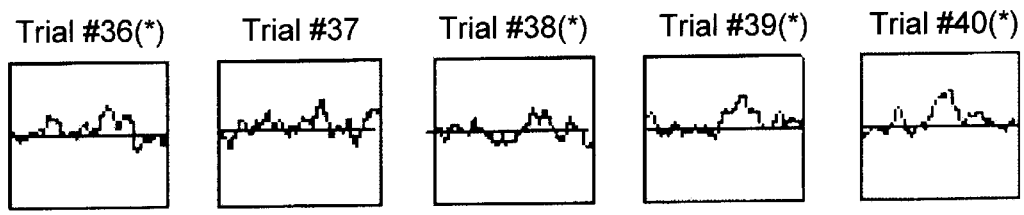

The wavelet coefficient surface output means 14 outputs wavelet coefficient $C_{a,b}$ obtained in the wavelet conversion means 13 as function values of scale parameter a and shift parameter b which are the parameters included in the wavelet conversion. However, as will be described later, this brain wave data processing device considers a three-dimensional space which makes the scale parameter and shift parameter to be xy-coordinate and the wavelet coefficient to be z-coordinate, and handles the function values as a surface within this three-dimensional space. This surface is referred to as a wavelet coefficient surface 121 (refer to FIGS. 6a and 6b). Accordingly, the wavelet coefficient window means 15 extracts a predetermined area from within the wavelet coefficient surface, the wavelet coefficient window parameter setting means 16 sets up the wavelet coefficient window according to the shapes and values of the wavelet coefficient surface, and the brain wave data discriminating means 17 discriminates whether a predetermined area is extracted in each wavelet coefficient surface when the wavelet coefficient surface corresponding to individual digital brain wave data is subjected to the wavelet coefficient window.

The operation of this brain wave data processing device will be described hereinbelow.

Firstly, the brain wave data derived and amplified from a subject by the electrodes for brain wave and the living signal amplifier which are the components of the brain wave data input means 11 are sampled by the A/D converter to be stored in the brain wave storage means 12 as the digital brain wave data. Next, the wavelet conversion means 13 converts the digital brain wave data according to the following expression:

$$C_{a,b} = \int_R s(t)\Psi\left(\frac{t-b}{a}\right)dt \frac{1}{\sqrt{a}}$$

where:
signal s(t) corresponds to the digital brain wave data;
$\Psi(t)$ is the mother wavelet;
a is the scale parameter;
b is the shift parameter; and
$C_{a,b}$ is referred to as the wavelet coefficient and can be regarded as the function of the scale parameter a and shift parameter b. The function values constituted a surface within the three-dimensional space in which the scale parameter a, the shift parameter b, and the wavelet coefficient $C_{a,b}$ compose a coordinate. In addition, this surface can express the function values as a gray scale on a plane created by the scale parameter and the shift parameter. The wavelet coefficient surface output means 14 outputs such a wavelet coefficient surface and its two-dimensional expression.

Figure 2A:
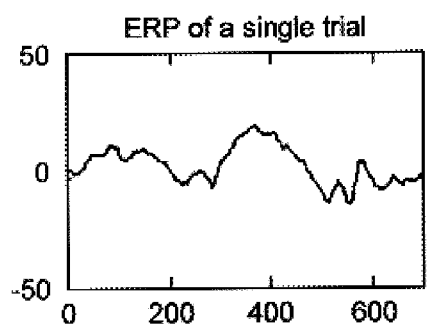
FIG. 2a shows an event-related potential (ERP) of a single trial in brain wave data.

FIG. 2a shows one example of the brain wave data in a single trial (an event-related potential in a visual oddball paradigm), and FIGS. 2b–2h show the output results of the wavelet coefficient surface output means 14 (the two-dimensional expressions of the wavelet coefficient surface) for seven kinds of mother wavelets (Mexican Hat, Morlet, Symlet (4), Daubechies (3), Haar, Meyer, and Coiflet (1)), respectively, when the brain wave data is subjected to the wavelet conversion. In these figures, the function values (wavelet coefficients) become higher as the color changes from black to white. It will be understood from these figures that the wavelet conversion which most significantly emphasizes distinguishing patterns in the brain wave data (positive components of latency of 300 ms to 500 ms) is the case when Mexican Hat is used for the mother wavelet. Thus, only the wavelet conversion in which Mexican Hat is made the mother wavelet will be treated hereinbelow. Incidentally, mother wavelet $\Psi(t)$ of Mexican Hat is designated by the following expression:

$$\Psi(t) = (1-t)^2 \exp\left(-\frac{|t|^2}{2}\right)$$

Figure 2B:
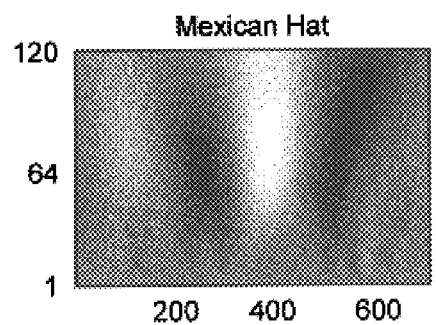
FIGS. 2b–2h show results of wavelet conversion of the brain wave data due to each different mother wavelet.
Figure 2C:
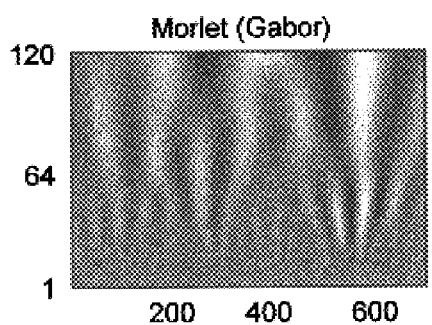
Figure 2D:
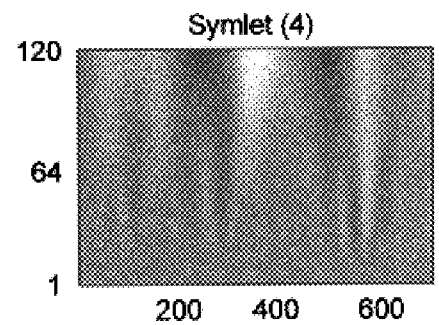
Figure 2E:
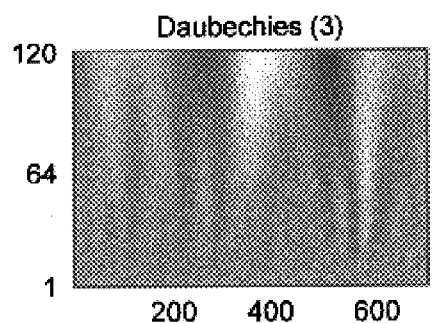
Figure 2F:
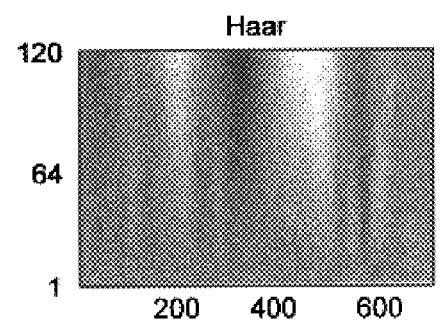
Figure 2G:
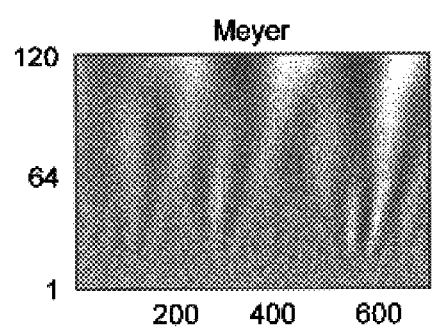
Figure 2H:
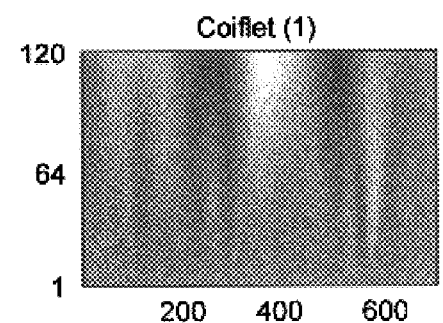

As is apparent from FIG. 2b, it will be appreciated that the area with high wavelet coefficients is a rectangle or ellipse contained by particular intervals of values of the scale parameter and shift parameters. In practice, when distinguishing patterns (P300 component) are detected by inspection in each brain wave data in a single trial, such a rectangular or elliptic area is discerned in the corresponding wavelet coefficient surface. FIG. 3a to FIG. 53a show event-related potentials (ERPs) in single trials from the first trial (Trial#1) to the fifty-first trial (Trial#51), and FIG. 3b to FIG. 53b show the corresponding wavelet coefficient surfaces. In these figures, "*" is attached to waveforms in which distinguishing patterns are detected. It is the wavelet coefficient window parameter setting means 16 that decides the shape of this rectangle or ellipse, and it is the wavelet coefficient window means 15 that extracts a predetermined area in the wavelet coefficient surface utilizing the set window.

Figure 54:
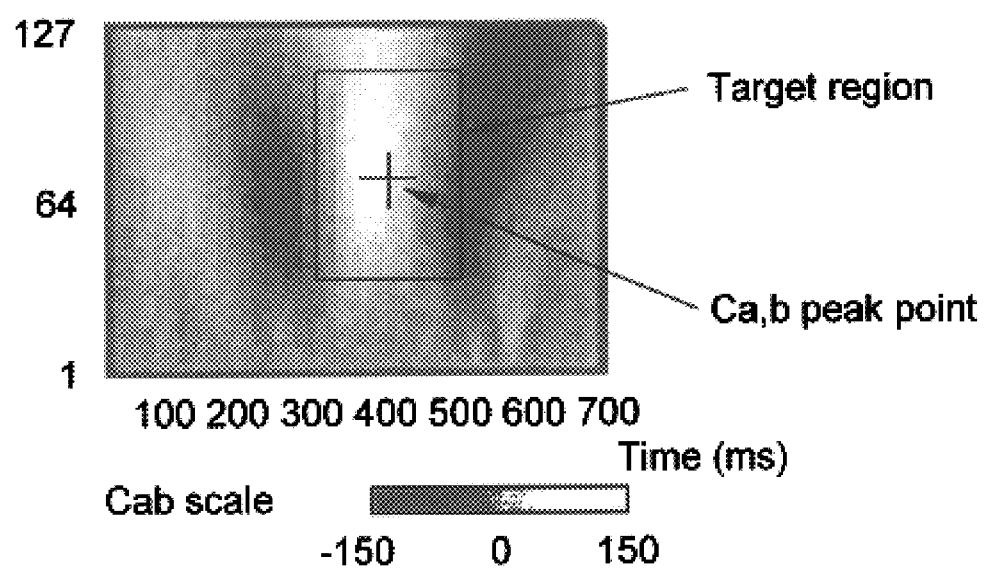
FIG. 54 illustrates a wavelet coefficient window and shows a rectangular window.
Figure 55A:
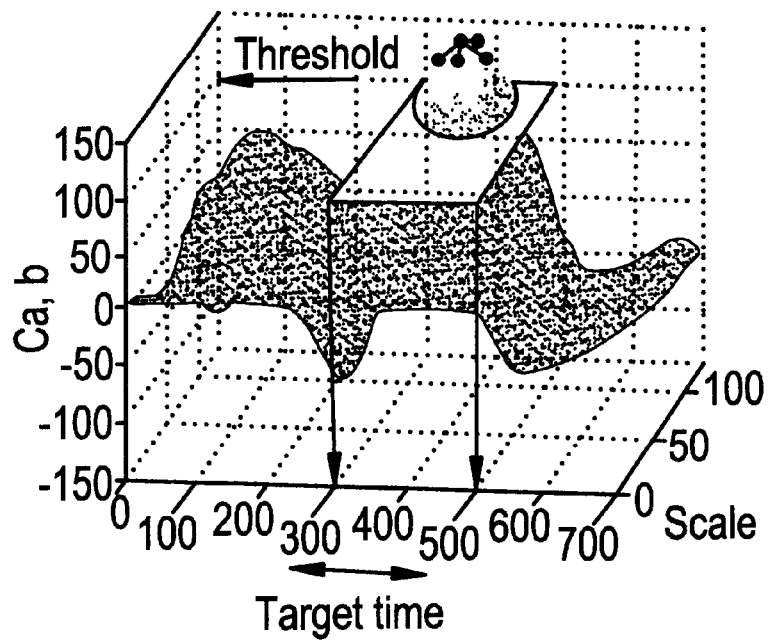
FIG. 55a shows a rectangular wavelet coefficient window.
Figure 55B:
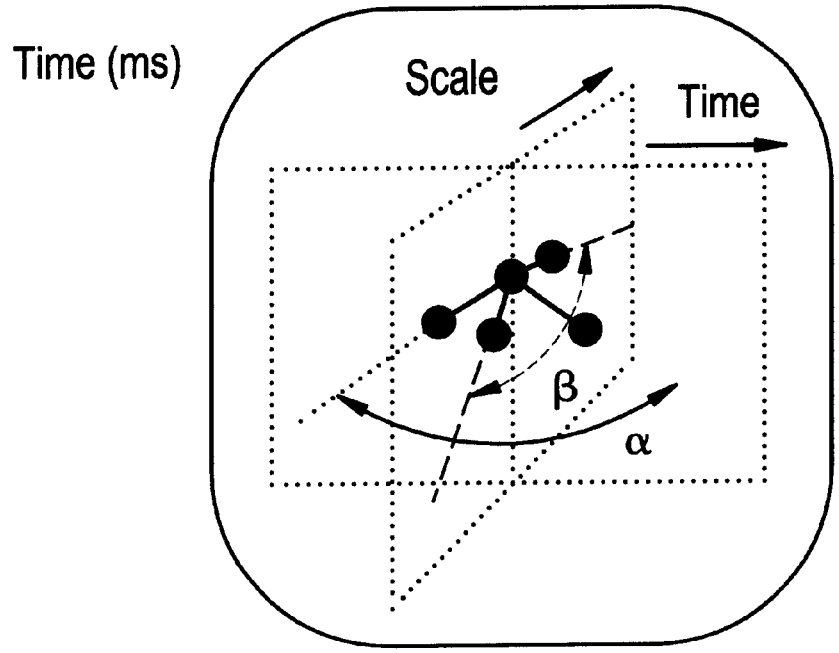

FIG. 54 illustrates a rectangular wavelet coefficient window. A rectangular area including a point with the maximum wavelet coefficient is set up in 40<a<110, and 300<b<500 (ms) in the figure. FIG. 55a illustrates an elliptic wavelet coefficient window, and FIG. 55b shows a partially enlarged portion of FIG. 55a. Firstly, a threshold of wavelet coefficient $C_{a,b}$ is determined (for example, 100). A cut surface due to this plane generally has an elliptic figuration, as with apparent from FIG. 54. Further, it is the brain wave data discriminating means 17 that discriminates whether a predetermined area is extracted in each wavelet coefficient surface when the wavelet coefficient surface corresponding to individual digital brain wave data is subjected to the wavelet coefficient window 15. If a predetermined area is extracted, the brain wave data is regarded to include distinguishing patterns, so that the brain wave data discriminating means 17 eventually discriminates existence of distinguishing patterns in individual brain wave data.

For example, in the case of FIG. 54, if the maximum value in the wavelet coefficient window exceeds a predetermined value (for example, 100), the brain wave data is judged to include distinguishing patterns. In addition, in the case of FIG. 55a and FIG. 55b, for the region cut out by the threshold plane, an angle α angled in the shift parameter plane and an angle β angled in the scale parameter plane with respect to lattice points in FIG. 55b are determined, and "if α<180°, β<180°, and the value of the wavelet coefficient at the central lattice point is larger than those of other lattice points", distinguishing patterns are judged to be detected.

This brain wave data processing device is capable of detecting only brain wave data with distinguishing patterns in the manner described above. Therefore, as with the second embodiment described below, averaging only brain wave data with distinguishing patterns can be automatically performed, and also, as in the case of the third embodiment, a vertex latency of a pattern in brain wave data with distinguishing patterns can be automatically determined.

Second Embodiment

Figure 56:
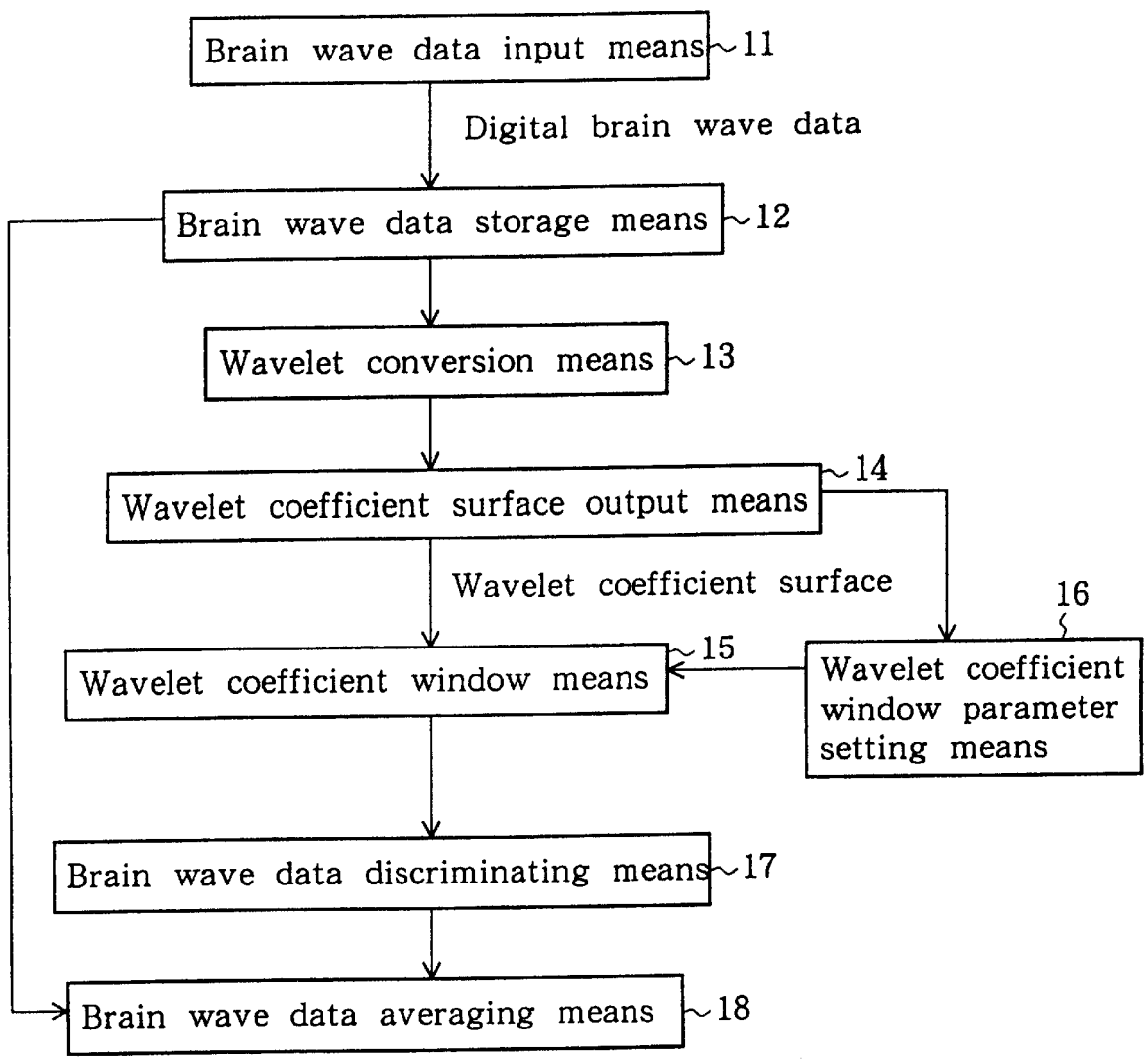
FIG. 56 is a block diagram showing a configuration of the brain wave data processing device of a second embodiment according to the present invention.

FIG. 56 is a block diagram showing a configuration of the brain wave data processing device of a second embodiment according to the present invention. The brain wave data processing device has a configuration in which a brain wave data averaging means 18 is added to the brain wave data processing device shown in FIG. 1. The brain wave data averaging means 18 adds only brain wave data discriminated to have distinguishing patterns in the brain wave data discriminating means 17 in synchronization with a trigger signal to determine the averaging. The trigger signal in this case means a signal which is occurred in synchronization with occurrence of excitations or events in trials for each trial. The brain wave data processing device according to the first embodiment can be constituted using a personal computer with the exception of the brain wave data input means 11, so the brain wave data averaging means 18 can also be realized by mounting such a program to a personal computer constituting the brain wave data processing device that executes the operation of the brain wave data averaging means 18, which will be described below.

The operation of the brain wave data processing device according to the second embodiment will be described hereinafter. In this brain wave data processing device, the components common to the brain wave data processing device of the first embodiment perform the same operation as in the device of the first embodiment, so that the explanation will be focused on the operation in the brain wave data averaging means 18. The brain wave data averaging means 18 reads out the only brain wave data judged to have distinguishing patterns in the brain wave data discriminating means 17 from the brain wave data storage means 12. Further, the trigger signal with respect to excitation is inputted to the brain wave data averaging means 18. The brain wave data averaging means 18 adds the brain wave data read out from the brain wave data storage means 12 in synchronization with the trigger signal to calculate and output the brain wave data. In this case, the brain wave data with distinguishing patterns refer to those from which a predetermined area is extracted in the wavelet coefficient surface, as described in the first embodiment.

Figure 57A:
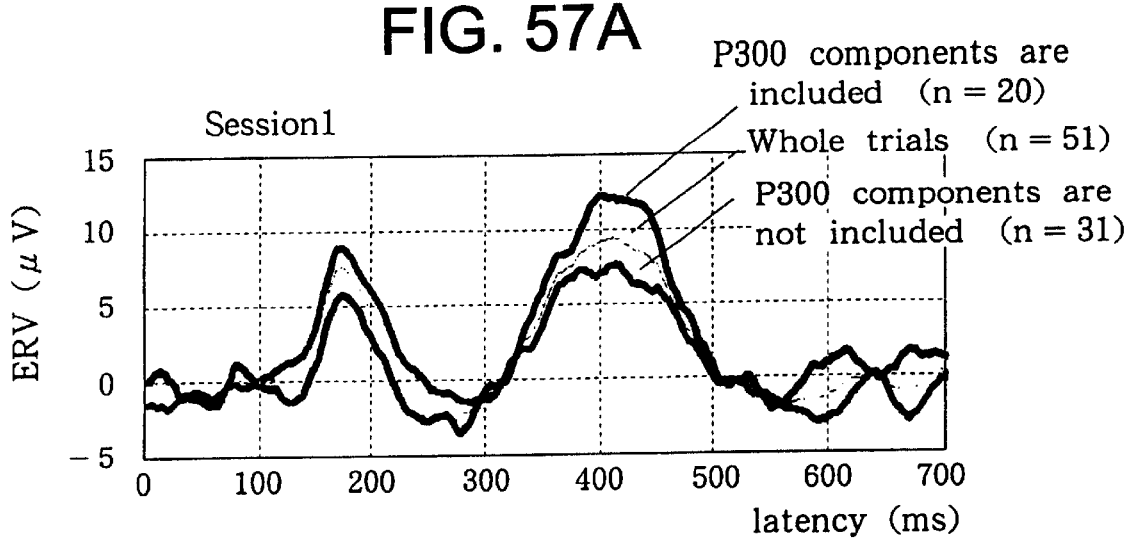
FIGS. 57a–57c are graphs showing results of processing the brain wave data in a single trial in the first, second, and third sessions using the averaging method, respectively.
Figure 57B:
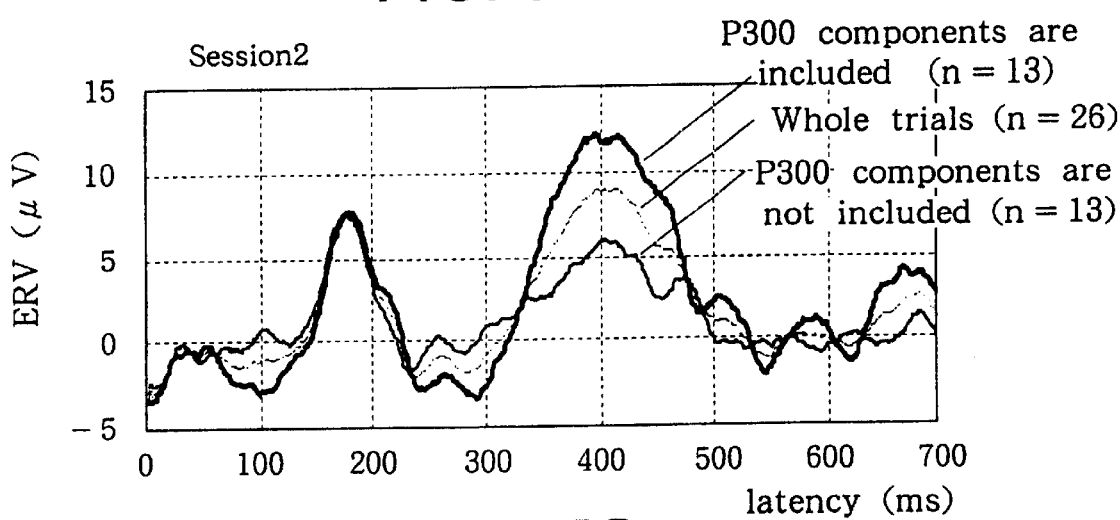
Figure 57C:
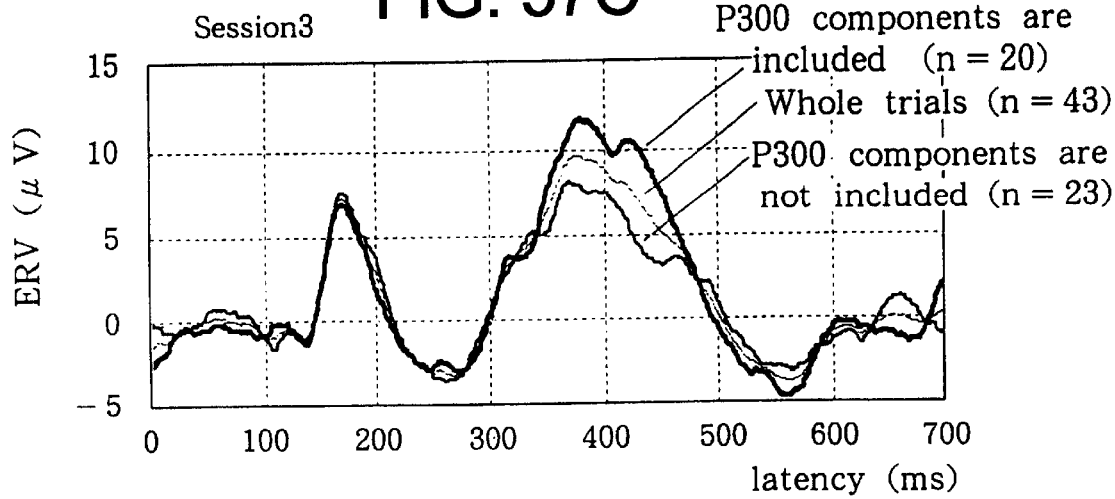

In the following, the results of averaging only the brain wave data with distinguishing patterns will be explained. Visual oddball exercise was performed for three sessions with breaks in mid course, and the brain wave data of individual single trial was averaged with three kinds of methods for each session. The visual oddball is such that, for example, three kinds of visual excitations (rare target: excitation frequency 20%; rare non-target: excitation frequency 20%; frequent non-target: excitation frequency 60%) are randomly exhibited to a subject and attention is made to be attracted only to rare target (for example, a button is made to be pressed only when a rare target is exhibited or number of exhibitions of the rare target is made to be reported to an experimenter after the experiment is over). FIG. 57*a* to FIG. 57*c* show the results of the averaging. FIG. 57*a*, FIG. 57*b*, and FIG. 57*c* show the result of the first, second, and third session, respectively, and the vertical axis is the event-related potential (ERP) and the horizontal axis is latency. Positive component with a latency approximately 300 ms (P300 component) is herein intended to be a distinguishing pattern. Curves of the results of averaging only brain wave data judged to include the distinguishing patterns (P300 components) by the brain wave data discriminating means 17, the results of averaging the brain wave data corresponding to all trials, and the results of averaging only brain wave data in which any distinguishing pattern can not be eminently detected are denoted in each figure. For example, in the case of FIG. 57*c* with respect to the third session, there are shown curves of the result of averaging all 43 trials, the result of averaging 20 trials in which distinguishing patterns are detected, and the result of averaging 23 trials in which distinguishing patterns are not detected. As will be apparent from this FIG. 57*c*, by averaging only brain wave data with distinguishing patterns, waveforms with the largest amplitude value can be obtained with respect to P300 components. On the contrary, positive components in latency between 150 and 200 ms hardly affect for decision regarding the target of averaging of brain wave data.

In this manner, in accordance with the brain wave data processing device of the second embodiment, all the processing from measurement of the brain wave data to averaging process can be automatically performed.

Third Embodiment

Figure 58:
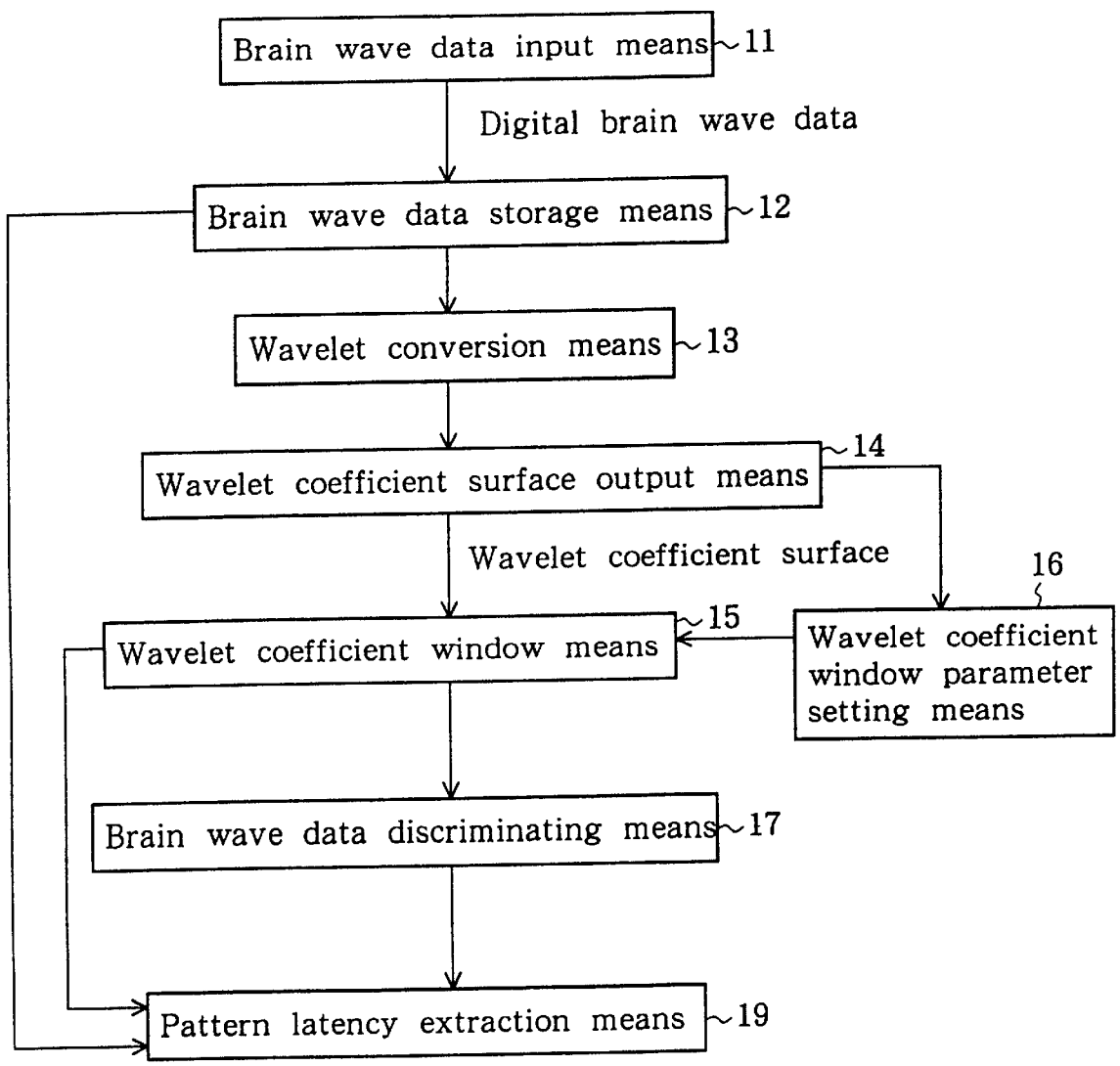
FIG. 58 is a block diagram showing a configuration of the brain wave data processing device of a third embodiment according to the present invention.

FIG. 58 is a block diagram showing a configuration of the brain wave data processing device of a third embodiment according to the present invention. The brain wave data processing device has a configuration in which a pattern latency extraction means 19 is added to the brain wave data processing device shown in FIG. 1. The pattern latency extraction means 19 determines a vertex latency (latency with the largest amplitude value of the brain wave data) of distinguishing patterns with respect to the only brain wave data judged to have the distinguishing patterns by the brain wave data discriminating means 17. The brain wave data processing device according to the first embodiment can be constituted using a personal computer with the exception of the brain wave data input means 11, so the pattern latency extraction means 19 can also be realized by mounting such a program to a personal computer constituting the brain wave data processing device that executes the operation of the pattern latency extraction means 19, which will be described below.

The operation of the brain wave data processing device according to the third embodiment will be described hereinafter. In this brain wave data processing device, the components common to the brain wave data processing device of the first embodiment perform the same operation as in the device of the first embodiment, so that the explanation will be focused on the operation in the pattern latency extraction means 19. The pattern latency extraction means 19 reads out the only brain wave data judged to have distinguishing patterns in the brain wave data discriminating means 17 from the brain wave data storage means 12, and determines a shift parameter value $b_{max}$ in which a value of the wavelet coefficient becomes maximum in an area set up by the wavelet coefficient window means 15. Then, in the read out digital brain wave data, it determines a latency in which the amplitude value of the brain wave data becomes maximum in a closed interval defined by $(b_{max}-t_b, b_{max}+t_b)$ with respect to a constant $t_b$.

Figure 59A:
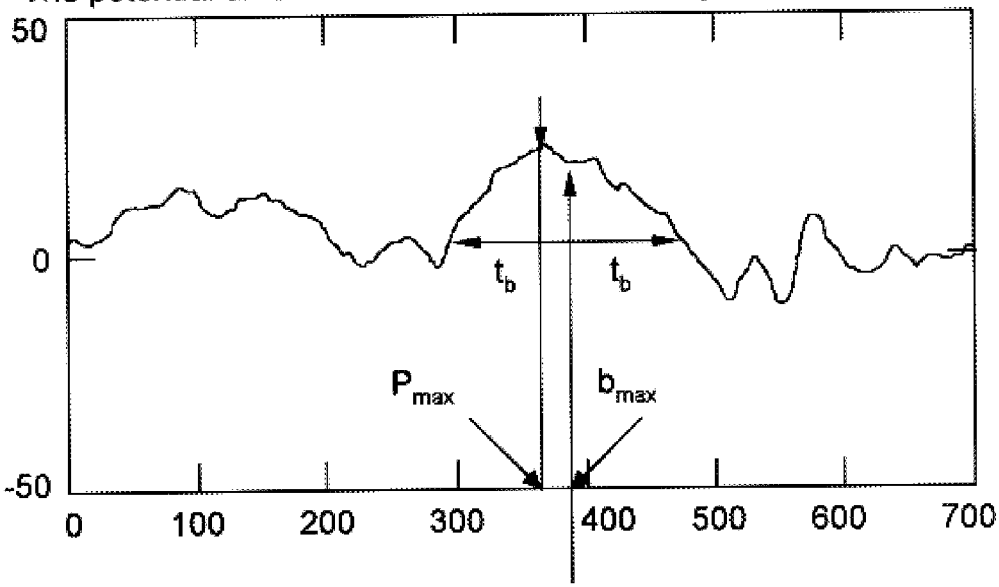
FIGS. 59a and 59b illustrate an extraction process of the pattern latency in the third embodiment according to the present invention.
Figure 59B:
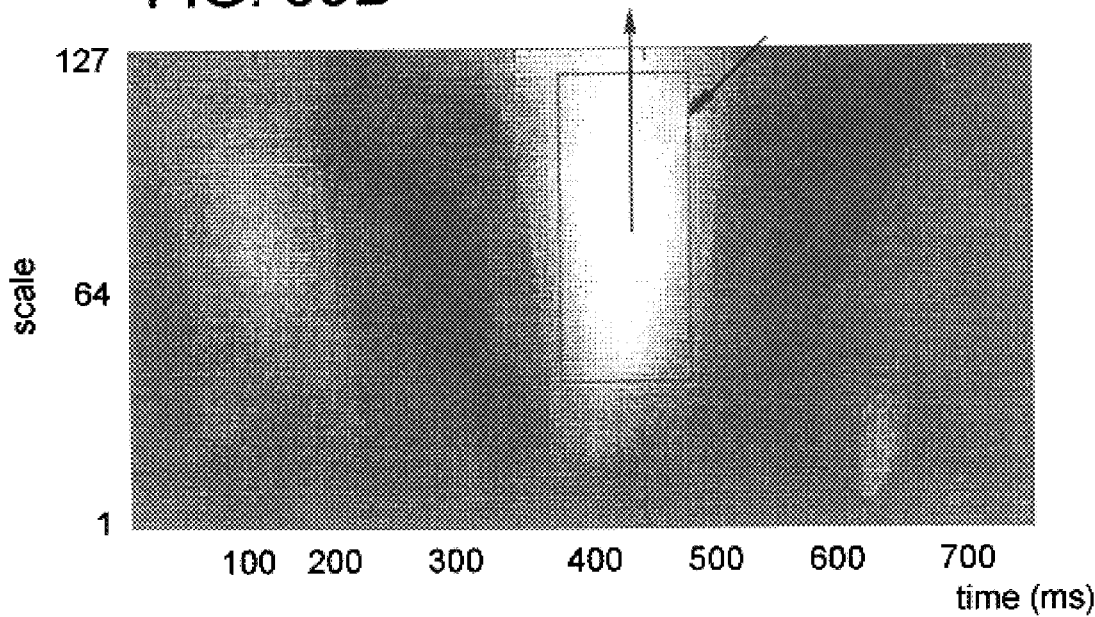

FIGS. 59*a* and 59*b* illustrate an extraction process of the latency due to the pattern latency extraction means 19. The waveform of FIG. 59*a* is the brain wave data of a single trial with respect to a rare target in a visual oddball exercise described above. The waveform of the brain wave data is subjected to the wavelet conversion to calculate a wavelet coefficient, the result of which is shown in FIG. 59*b*. In FIG. 59*b*, when the wavelet coefficient window is set up to the designated rectangular area, a shift parameter value $b_{max}$ is specified in which a value of the wavelet coefficient becomes maximum in the area of the set wavelet coefficient window. And, as shown in FIG. 59*a*, when a latency is determined in which an amplitude value of the brain wave data becomes maximum with respect to a constant tb (for example, 50 ms) in a closed interval defined by $(b_{max}-t_b, b_{max}+t_b)$, vertex latency Pmax of P300 component can be obtained.

By providing the pattern latency extraction means 19 in this way, the vertex latency of the extracted pattern can be automatically determined. Furthermore, by combining it with the brain wave data averaging means used in the second embodiment, the vertex latency of the pattern can be determined from the result of averaging only brain wave data with distinguishing patterns, allowing the accuracy of the measurement of the vertex latency to be improved.

Configuration by a Personal Computer

Figure 60:
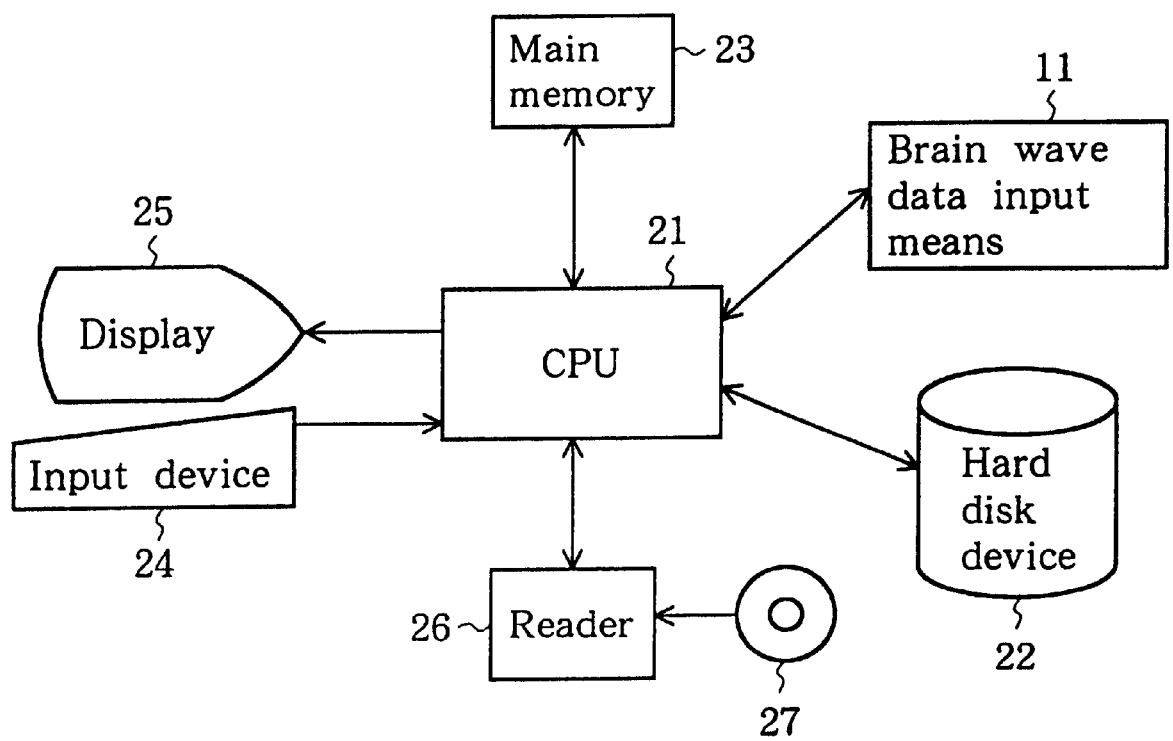
FIG. 60 is a block diagram showing a configuration of a personal computer composing the brain wave data processing device.

As described above, the brain wave data processing device of each embodiment can also be realized by using a computer system such as a personal computer, installing a program to realize the brain wave data processing device to the computer system, and executing the program. The program to realize the brain wave data processing device is read in the computer system by a storage medium such as a magnetic tape and CD-ROM. Supposing that the brain wave data processing device is herein composed of a personal computer, the personal computer will be explained. FIG. 60 is a block diagram showing a configuration of a personal computer composing the brain wave data processing device.

The personal computer is composed of a CPU (central processing unit) 21, a hard disk device 22 for storing a program and data (particularly, digital brain wave data), a main memory 23, an input device 24 such as a keyboard and mouse, a display 25 such as a CRT, and a reader 26 for reading a storage medium such as a magnetic tape and CD-ROM, and a brain wave data input means 11 is connected to the computer. The brain wave data input means 11 is typically composed of a combination of electrodes for brain wave, a living signal amplifier, and an A/D conversion board, and the A/D conversion board is inserted into an expansion slot (not shown) of the personal computer, so that it is connected to the CPU 21 through an internal bus (not shown) of the personal computer. In addition, each of the hard disk device 22, the main memory 23, the input device 24, the display 25, and the reader 26 is connected to the CPU 21. In the personal computer, the storage medium 27 in which the program for realizing the brain wave data processing device described above is stored is mounted to the reader 26, the program is read out from the storage medium 27 to be stored in the hard disk device 22, and the program stored in the hard disk device 22 is executed by the CPU 21, so that each processing on the brain wave data processing device is performed, causing the brain wave data processing device to be realized.

As discussed above, the present invention is preferable to extract the peak components in which the wavelet conversion is temporally located, and also, as it seeks whole of the wavelet coefficients (the wavelet coefficient surface) during extraction, the information of the original brain wave waveform are hardly lost, so that the present invention has the effect of extracting distinguishing patterns from the brain waves of a single trial without inspection of an experimenter.

Further, the distinguishing patterns can be detected from the brain waves of a single trial, allowing the brain wave data for a target of averaging to be discriminated automatically, so that the present invention has the effects such that the waveform derived from averaging brain wave data can be precisely obtained, and moreover, the vertex latency of distinguishing patterns of the brain waves of a single trial can be determined.

According to the present invention, the vertex latency of P300 components can be determined from, for example, event-related potential data in a single trial, so that improvement of accuracy and real-time property of higher order brain function test and definition of relationship with other test indicators such as an autonomic nervous system indicator can be realized.

What is claimed is:

1. A brain wave data processing device detecting distinguishing patterns from individual brain wave data obtained in a single trial, said brain wave data processing device comprising:

a brain wave data storage means for storing digital brain wave data;

a wavelet conversion means for subjecting said digital brain wave data read out from said brain wave data storage means to wavelet conversion to determine a wavelet coefficient;

a wavelet coefficient surface output means for outputting said wavelet coefficient as function values of a scale parameter and a shift parameter in said wavelet conversion;

a wavelet coefficient window parameter setting means for setting a wavelet coefficient window;

a wavelet coefficient window means for extracting a predetermined area based on said wavelet coefficient window from a wavelet coefficient surface defined by said scale parameter, said shift parameter, and said wavelet coefficient; and a brain wave data discriminating means for discriminating whether or not said predetermined area has been extracted from said wavelet coefficient surface by said wavelet coefficient window means for individual digital brain wave data.

2. The brain wave data processing device according to claim 1, further comprising electrodes for brain wave, an amplifier for amplifying feeble signals measured by said electrodes for brain wave, and an analog-digital converter for converting analog brain wave data outputted from said amplifier to digital brain wave data.

3. The brain wave data processing device according to claim 1, wherein said wavelet coefficient window is set based on a wavelet coefficient surface corresponding to brain wave data from which distinguishing patterns are detected.

4. The brain wave data processing device according to claim 1, wherein Mexican Hat is used as a mother wavelet in said wavelet conversion.

5. The brain wave data processing device according to claim 1, further comprising a brain wave data averaging means for averaging only digital brain wave data from which said predetermined area is extracted in said wavelet coefficient surface.

6. The brain wave data processing device according to claim 1, further comprising a pattern latency extraction means for determining a vertex latency of distinguishing patterns included only in digital brain wave data from which said predetermined area is extracted in said wavelet coefficient surface.

7. A storage medium in which individual digital brain wave data due to a single trial is inputted and which can be read out by a computer, said storage medium comprising a computer program, the computer program comprising instructions which, when executed, perform:

a function for subjecting said digital brain wave data to wavelet conversion to determine a wavelet coefficient;

a function for determining said wavelet coefficient as function values of a scale parameter and a shift parameter in said wavelet conversion;

a function for setting a wavelet coefficient window;

a function for extracting a predetermined area based on said wavelet coefficient window from a wavelet coefficient surface defined by said scale parameter, said shift parameter, and said wavelet coefficient; and a function for discriminating whether said predetermined area is extracted from said wavelet coefficient surface for each individual brain wave data.

8. The storage medium according to claim 7, wherein said instructions of said program further perform a function for adding and averaging only digital brain wave data from which said predetermined area is extracted.

9. The storage medium according to claim 7, wherein said instructions of said program further perform a function for determining a vertex latency of distinguishing patterns included only in digital brain wave data from which said predetermined area is extracted.

* * * * *